United States Patent [19]
Van Der Puy et al.

[11] Patent Number: 5,632,966
[45] Date of Patent: May 27, 1997

[54] PROCESS FOR HYDROGEN FLUORIDE SEPARATION

[75] Inventors: Michael Van Der Puy, Amherst; Mathew H. Luly, Lancaster, both of N.Y.

[73] Assignee: AlliedSignal Inc., Morris County, N.J.

[21] Appl. No.: 612,048

[22] Filed: Mar. 7, 1996

[51] Int. Cl.$^6$ .................................................. C01B 7/19
[52] U.S. Cl. ...................... 423/484; 423/483; 423/488; 423/462; 423/240 R
[58] Field of Search .......................... 423/484, 483, 423/240 R, 488, 462

[56] References Cited

U.S. PATENT DOCUMENTS

| | | | |
|---|---|---|---|
| 3,591,432 | 7/1971 | Vazirani | 156/3 |
| 3,873,629 | 3/1975 | Jones | 260/653 |
| 3,935,097 | 1/1976 | Roof | 210/31 C |
| 3,947,558 | 3/1976 | Van Eijl | 423/483 |
| 3,976,447 | 8/1976 | Merchant et al. | 55/71 |
| 4,209,470 | 6/1980 | Lorquet | 260/652 |
| 4,210,460 | 7/1980 | Seidenberger | 134/7 |
| 4,297,257 | 10/1981 | Elias et al. | 260/29.6 |
| 4,373,050 | 2/1983 | Steinbrecher et al. | 524/405 |
| 4,640,831 | 2/1987 | DeVries | 423/481 |
| 4,882,134 | 11/1989 | Mizrahi | 423/356 |
| 4,902,312 | 2/1990 | Chang | 55/71 |
| 4,943,360 | 7/1990 | Sugisawa et al. | 204/182.3 |
| 4,999,095 | 3/1991 | Chlanda et al. | 204/182.4 |
| 5,032,371 | 7/1991 | Buehler | 423/484 |
| 5,139,632 | 8/1992 | Chlanda et al. | 204/182.4 |
| 5,211,020 | 5/1993 | Taylor et al. | 62/11 |
| 5,211,817 | 5/1993 | Adams et al. | 203/82 |
| 5,300,709 | 4/1994 | Eicher et al. | 570/164 |
| 5,336,832 | 8/1994 | Keller | 585/710 |

OTHER PUBLICATIONS

*Chemical Abstracts* 120:57882q (1994) for Russian Patent No. 1,566,651 of Molokhov et al. entitled "Manufacture of Gaseous Hydrogen Fluoride".

Jache, Albert W. and Cady, George H. "Solubility of Fluorides of Metals in Liquid Hydrogen Fluoride" *J. Phys. Chem.* 56 (1952) 1106.

*Primary Examiner*—Deborah Jones
*Assistant Examiner*—Amy M. Harding
*Attorney, Agent, or Firm*—Lois A. Gianneschi

[57] ABSTRACT

The present invention provides a convenient method for separating hydrogen fluoride from a chemical mixture. More specifically, a method is provided in which hydrogen fluoride is separated from a chemical mixture containing at least one organic material by contacting the chemical mixture with a hydrogen fluoride binder. The hydrogen fluoride separated from the chemical mixture is readily recoverable from the hydrogen fluoride binder.

19 Claims, No Drawings

PROCESS FOR HYDROGEN FLUORIDE SEPARATION

FIELD OF THE INVENTION

The present invention relates to a method for separating hydrogen fluoride from a chemical mixture. More specifically, a method is provided for separating hydrogen fluoride from a chemical mixture containing hydrogen fluoride and at least one organic material.

BACKGROUND OF THE INVENTION

Hydrogen fluoride is widely used by industry in a variety of processes. For example, hydrogen fluoride is used in fluorocarbon manufacture. In such processes, it is desirable to separate the hydrogen fluoride from the reactants and products. However, hydrogen fluoride can be difficult to separate in these processes because it is highly soluble in a variety of organic materials and may form azeotropic mixtures with these materials.

A number of methods have been developed for separating hydrogen fluoride from organic materials. For example, separation of hydrogen fluoride from a hydrogen fluoride-organic azeotropic composition using water is known. However, this method is disadvantageous because hydrogen fluoride forms an azeotropic composition with water making recovery of the hydrogen fluoride difficult.

U.S. Pat. No. 5,336,832 discloses the separation of hydrogen fluoride from a hydrocarbon stream by passing the stream over a sodium fluoride bed. This method is energy intensive in that high temperatures are required to liberate the hydrogen fluoride from the sodium fluoride bed.

Other known methods include the use of sulfuric acid, alkaline earth compounds, molecular sieves, distillation, and membranes to facilitate separation of the hydrogen fluoride. However, each of these known methods is disadvantageous in that these processes are inefficient or costly to operate. Thus, a need exists for a process for separating hydrogen fluoride from organic materials that does not suffer from the disadvantages of the prior art methods.

DESCRIPTION OF THE INVENTION AND PREFERRED EMBODIMENTS

This invention provides a continuous, intermittent, or batch process for separating hydrogen fluoride from a chemical mixture containing hydrogen fluoride and at least one organic material. The process of the invention provides a convenient and cost-effective method for separating hydrogen fluoride.

For purposes of this invention, separation includes both the isolation of hydrogen fluoride from a mixture as well as the removal of impurities from hydrogen fluoride. Organic material, for purposes of this invention, include halocarbons such as chlorofluorocarbons, hydrochlorofluorocarbons, fluorocarbons, hydrofluorocarbons, hydrocarbons, chlorocarbons, fluoroethers, alcohols, ketones, and mixtures thereof. The organic materials most suitable for use in the process of this invention are halocarbons such as chlorofluorocarbons, hydrochlorofluorocarbons, fluorocarbons, hydrofluorocarbons, hydrocarbons, chlorocarbons, fluoroethers, and mixtures thereof.

The process of the invention comprises the steps of: (A) contacting a chemical mixture containing hydrogen fluoride and at least one organic material with a hydrogen fluoride binder, which binder comprises a liquid mixture of an acid salt and hydrogen fluoride, under conditions suitable to produce a mixture having a binder phase, comprising a mixture of hydrogen fluoride extracted from the chemical mixture and the binder, and an organic phase; (B) separating the binder phase from the mixture: (C) and recovering the hydrogen fluoride extracted from the chemical mixture from the binder phase. In another embodiment of the invention, after separation of the binder phase, the binder phase is used in a hydrogen fluoride-requiring reaction. By hydrogen fluoride-requiring reaction is meant any reaction in which hydrogen fluoride is used or is a reactant. In yet another embodiment, the hydrogen fluoride binder is recycled to step (A) following step (C).

The process of the invention may be carried out in any suitable corrosion resistant vessel. Step (A) of the process of the invention comprises contacting the chemical mixture, containing hydrogen fluoride and at least one organic material, with a hydrogen fluoride binder. The hydrogen fluoride and organic material may form an azeotropic composition. Further, the chemical mixture may be in liquid or gaseous phase.

Contacting may be carried out by any convenient means known in the art. For example, for liquid phase chemical mixtures at room temperature, contacting may be achieved by shaking or stirring the mixture. For chemical mixtures with boiling points below room temperature, contacting may be performed by passing the vapors of the chemical mixture over or through the binder. Because the binder itself contains hydrogen fluoride as its most volatile component, the vapor pressure of the binder will be due mainly to hydrogen fluoride, which vapor pressure increases with increases in temperature. Thus, the contacting preferably is accomplished at temperatures from about 0° C. to about 25° C. to optimize removal of hydrogen fluoride from the chemical mixture.

Contacting of the chemical mixture with the hydrogen fluoride binder in step (A) produces a mixture having two phases: (i) a binder phase that is a mixture of the binder and hydrogen fluoride extracted from the chemical mixture; and (ii) an organic phase. It will be apparent that the hydrogen fluoride content of the binder, which is initially low, increases as step (A) proceeds. Step (A) preferably proceeds until the effective capacity of the hydrogen fluoride binder is approximated. The effective capacity of the binder is approximated when it is determined that the hydrogen fluoride is no longer being extracted from the chemical mixture at the desired level. From an efficiency standpoint, it is preferred that step (A) proceed until the effective capacity of the binder is approximated, which approximation will facilitate step (C). This is because, the lower the weight percent of extracted hydrogen fluoride in the binder, the higher the temperature that will be required to remove the extracted hydrogen fluoride from the binder.

In step (B), the binder phase is separated from the mixture produced in step (A) and, in step (C), the hydrogen fluoride extracted from the chemical mixture is recovered from the binder phase. In step (B) of the process of the invention, the binder phase is separated from the mixture of step (A) by any method well known in the art. This generally will be easily accomplished given that the most suitable organic materials for use in the process of the invention are non-basic materials that will be insoluble, or only slightly soluble, in the binder phase. One ordinarily skilled in the art will appreciate that the solubility of the organic material in the binder phase will be a function of the temperature and the weight percent of hydrogen fluoride in that phase. For the organic material most suited for the process of the invention, solubilities of less than about 10 weight percent in the binder phase are readily achieved.

The hydrogen fluoride extracted from the chemical mixture is recovered in step (C) by heating the binder phase to liberate hydrogen fluoride vapor and then condensing the hydrogen fluoride vapor. Recovery of the hydrogen fluoride may be performed at a temperature of about 100° C. or less. Although pressure is not critical, the recovery is preferably performed at subatmospheric pressure to facilitate hydrogen fluoride recovery. Further, because it is desirable, from a convenience standpoint, to maintain a liquid binder throughout steps (A) though (C), preferably sufficient hydrogen fluoride should be retained in the binder to maintain a liquid binder. Preferably, hydrogen fluoride is recovered in step (C) until the hydrogen fluoride in the binder phase is approximately that of the binder used in step (A).

In an alternative embodiment of the invention, in step (C) the fluorine value of the binder phase separated in step (B) is recovered by using the binder phase in a hydrogen fluoride-requiring reaction. Exemplary hydrogen fluoride-requiring reactions include, without limitation, alkylation and fluorination reactions.

The hydrogen fluoride binder used in the process of the invention is a liquid mixture of an acid salt and hydrogen fluoride, the hydrogen fluoride binder being capable of extracting and reversibly binding the hydrogen fluoride in the chemical stream without permanently altering the chemical properties of the hydrogen fluoride. Acid salts suitable for use in the hydrogen fluoride binder are salts of acids which acids have a $pK_a$ of about 4 or less, preferably of about 0 or less which acids are liquid at room temperature and are soluble in hydrogen fluoride.

Suitable acids include, without limitation, carboxylic acids, sulfonic acids and inorganic acids such as sulfuric, phosphoric, nitric acids, and mixtures thereof. Preferably, the acid is difluoroacetic, trifluoroacetic, formic, methanesulfonic, benzenesulfonic, toluenesulfonic, trifluoromethanesulfonic, fluorosulfonic, sulfuric acid and the like. More preferably, the acid is trifluoroacetic, sulfuric, or methanesulfonic acids. The acid salt counterion may be any counterion that forms a salt with the acid selected which salt is soluble in hydrogen fluoride. By soluble in hydrogen fluoride is meant that the acid salt dissolves, or forms homogeneous solution, with hydrogen fluoride in about ten times its weight or less of hydrogen fluoride. The acid salt counterion may be ammonium, an alkyl ammonium such as tetramethyl- or tetraethylammonium, or an alkali metal (Group IA) cation. Preferably, the counterion is ammonium cation. The preferred acid salts are ammonium trifluoroacetate, ammonium sulfate, and ammonium methanesulfonate.

To prepare the hydrogen fluoride binder of the invention, the acid salt is dissolved in an effective amount of hydrogen fluoride. Alternatively, the acid salt may be formed in situ by mixing together the acid, a bifluoride salt, and hydrogen fluoride.

One ordinarily skilled in the art will recognize that the ability of the binder to remove hydrogen fluoride from the chemical mixture will depend on the hydrogen fluoride content of the binder and, thus, binders having low hydrogen fluoride content will have the greatest capacity and efficiency for hydrogen fluoride separation from the chemical mixture. Therefore, acid salts requiring only very small amounts of hydrogen fluoride to dissolve are preferred.

The hydrogen fluoride used in the binder is commercially available anhydrous hydrogen fluoride with a water content of less than 0.1%. Similarly, the acid salt is preferably substantially anhydrous, or having a water content of less than about 1%, some of which salts are commercially available. Alternatively, substantially anhydrous acid salts may be produced by using any of the well known drying techniques such as desiccant or vacuum drying. Further, if the desired salt is not readily available or is expensive, the salt may be prepared by mixing the acid with a bifluoride salt to form the acid salt.

Advantageously, the effective amount of hydrogen fluoride is as small amount as possible yet is an amount that is effective to dissolve the acid salt to form a binder that is a liquid mixture of acid salt and hydrogen fluoride. The specific amount of hydrogen fluoride used to prepare the hydrogen fluoride binder will depend on the acid salt selected. The lower limit of the amount of hydrogen fluoride used is based on the solubility of the selected acid salt in hydrogen fluoride, which solubility may be readily determined by estimating or measuring the solubility of the acid salt in hydrogen fluoride. Generally, from about 20 to about 80 weight percent, preferably from about 22 to about 70 weight percent, of hydrogen fluoride is used. For the preferred acid salts, the following amounts of hydrogen fluoride are preferred: about 24 weight percent hydrogen fluoride for the HF/ammonium trifluoroacetate binder; about 27 weight percent hydrogen fluoride for the HF/ammonium methanesulfonate binder; and about 33 weight percent hydrogen fluoride for the HF/ammonium sulfate binder.

The invention will be clarified further through a consideration of the following examples that are meant to be purely exemplary.

EXAMPLES

Example 1

A binder of 34 weight percent, 15.2 g, HF and 66 weight percent ammonium sulfate was contacted with 25.35 g $CF_3CF_2CH_2CH_2F$ which is miscible and forms an azeotrope with HF. The upper layer was separated and its HF content determined by titration. Analysis indicated that the weight percent HF in the organic layer was only 0.06%.

Example 1 demonstrates that hydrogen fluoride is tightly bound by the binder used in the process of this invention.

Example 2

28.2 g of a $HF/CF_3CF_2CH_2CH_2F$ mixture containing 16.9 wt % HF was shaken with 33.9 g of a second liquid mixture of equimolar amounts of methanesulfonic acid and ammonium bifluoride (equivalent to 26.1 weight percent HF, assuming the fluorine is present as HF). The two phase mixture was stored in a refrigerator while allowing the phases to separate. The bottom organic layer was separated and the HF content determined by titration. Titration indicated that the HF content in the $CF_3CF_2CH_2CH_2F$ was reduced to 0.32 wt %, corresponding to the removal of 98% of the HF.

Example 3

To simulate recovery of extracted HF from the binder phase, a cylinder containing a mixture of 60.9 wt % HF and 39.1 wt % ammonium methanesulfonate was connected to a receiver cooled to −78° C. The cylinder containing the mixture was heated to 50°±5° C. for 40 minutes during which time 7.9 g HF was transferred to the receiver, corresponding to 47% of the HF present in the original mixture.

Example 4

Qualitative solubility tests were performed to determine which combinations of fluoride salt and acid resulted in a homogeneous solution over a wide range of weight percentages of HF. These mixtures, such as ammonium bifluoride in trifluoroacetic acid may also be thought of as the salt of the acid, i.e., ammonium trifluoroacetate, dissolved in two moles of HF. The data in Table 1 indicate whether or not the fluoride salts dissolved completely in various acids at approximately 25° C. The data indicate that ammonium salts are particularly soluble in strong acids, $pK_a$ of about 0 or less. The calculated weight percentage of HF, assuming all of the fluorine is present as HF, was 23.4%. Formic acid, $pK_a$ 3.75, was found to be a good solvent, better than the weaker acetic acid, $pK_a$ 4.75, but not as good as the stronger acids such as methanesulfonic, $pK_a$ approximately −3, trifluoroacetic, $pK_a$ 0.2, or sulfuric acid, $pK_a$ approximately −3.

TABLE 1

| Acid | LiF 2:1* | KHF$_2$ 2:1 | KHF$_2$ 1:1 | NH$_4$HF$_2$ 2:1 | NH$_4$HF$_2$ 1:1 | NH$_4$HF$_2$ 1:2 |
|---|---|---|---|---|---|---|
| CH$_3$SO$_3$H | — | — | NO | — | — | YES | — |
| CF$_3$COOH | — | NO | NO | — | — | YES | — |
| CH$_3$COOH | — | — | NO | — | NO | — | — |
| H$_2$SO$_4$ | NO | — | — | NO | — | YES | YES |
| HCOOH | — | — | YES | NO | YES | NO | — |

*Ratios indicate the acid to salt mole ratio.

Example 4 demonstrates that ammonium salts are particularly soluble in strong acids, $pK_a$ about 4 or less.

Example 5

2.21 g 2,6-dichlorobenzoyl chloride was dissolved in 5 mL cyclohexane. To this was added 3.7 g of a 64 wt % HF/36 wt % CF$_3$COONH$_4$. The two phase system was stirred vigorously at room temperature for 4 hours. Gas chromatograph analysis indicated complete conversion and only one product peak. The mixture was diluted with 5 mL cyclohexane and the upper layer was separated from the lower layer. The lower layer was washed twice with 5 mL cyclohexane and the combined cyclohexane layers treated with a small amount of KF. After filtering the KF, volatiles were removed under vacuum to yield 1.86 g, 92% yield, of 99% pure 2,3-dichlorobenzoyl fluoride.

Example 5 demonstrates the recovery of fluorine value from the binder phase by using the binder phase for the fluorination of 2,6-dichlorobenzoyl chloride.

Example 6

A binder composed of 24.1 weight percent HF and 75.9 weight percent ammonium methanesulfonate was prepared. An azeotropic mixture of CH$_3$CFCl$_2$ (HCFC-141b) and HF containing 0.43 wt % HF was prepared and 1.00 g of the binder was stirred for 15 min at room temperature with 61.9 g of the azeotropic mixture. The HF content in the HCFC-141b phase was determined by titration to be 0.021 wt % HF corresponding to the removal of 95% of the HF from the HCFC-141b. The HF-binder phase was calculated to contain 39 wt % HF.

Example 6 demonstrates the use of the binder of the invention to separate from an HF/HCFC azeotrope.

What is claimed is:

1. A process for separating hydrogen fluoride from a chemical mixture containing hydrogen fluoride and at least one organic material comprising the steps of:

(A) contacting the chemical mixture with a hydrogen fluoride binder, comprising hydrogen fluoride and an acid salt, under conditions suitable to produce a mixture having (i) a binder phase comprising hydrogen fluoride extracted from the chemical mixture and the hydrogen fluoride binder and (ii) an organic phase;

(B) separating the binder phase from the mixture produced in step (A); and (C) recovering the hydrogen fluoride extracted from the chemical mixture from the binder phase.

2. The process of claim 1 wherein step (C) comprises recovering the hydrogen fluoride from the binder phase separated in step (B) by using the binder phase in a hydrogen fluoride-requiring reaction.

3. The process of claim 1 further comprising step (D) recycling the binder to step (A) following step (C).

4. The process of claim 1 wherein the hydrogen fluoride in the binder is an amount from about 20 weight percent to about 85 weight percent based on the total weight of the binder.

5. The process of claim 4 wherein the hydrogen fluoride in the binder is present in an amount from about 22 weight percent to about 70 weight percent based on the total weight of the binder.

6. The process of claim 4 wherein the acid salt is a salt of a liquid acid having a $pK_a$ of about 4 or less.

7. The process of claim 6 wherein the acid is a carboxylic acid, a sulfonic acid, an inorganic acid, or mixtures thereof.

8. The process of claim 7 wherein the carboxylic acid is formic or trifluoroacetic acid.

9. The process of claim 7 wherein the carboxylic acid is trifluoroacetic acid.

10. The process of claim 7 wherein the sulfonic acid is methanesulfonic or trifluoromethanesulfonic acid.

11. The process of claim 7 wherein the sulfonic acid is methanesulfonic acid.

12. The process of claim 7 wherein the inorganic acid is sulfuric, phosphoric, or nitric acid.

13. The process of claim 7 wherein the inorganic acid is sulfuric acid.

14. The process of claim 6 wherein the salt is an ammonium salt.

15. The process of claim 1 wherein the acid salt is ammonium trifluoroacetate and the hydrogen fluoride is present in an amount of at least about 24 weight percent based on the total weight of the binder.

16. The process of claim 1 wherein the acid salt is ammonium sulfate and the hydrogen fluoride is present in an amount of at least about 33 weight percent based on the total weight of the binder.

17. The process of claim 1 wherein the acid salt is ammonium methanesulfonate and the hydrogen fluoride is present in an amount of at least about 27 weight percent based on the total weight of the binder.

18. The process of claim 2 wherein the hydrogen fluoride-requiring reaction is a fluorination reaction.

19. The process of claim 2 wherein the hydrogen fluoride-requiring reaction is an alkylation reaction.

* * * * *

UNITED STATES PATENT AND TRADEMARK OFFICE
CERTIFICATE OF CORRECTION

PATENT NO. : 5,632,966
DATED : May 27, 1997
INVENTOR(S) : Van Der Puy et al.

It is certified that error appears in the above-identified patent and that said Letters Patent is hereby corrected as shown below:

Column 5, line 60, after "separate", insert -- HF --.

Signed and Sealed this

Twenty-first Day of December, 1999

Attest:

Q. TODD DICKINSON

*Attesting Officer*   *Acting Commissioner of Patents and Trademarks*